United States Patent [19]

Ibar

[11] Patent Number: 5,152,607

[45] Date of Patent: Oct. 6, 1992

[54] PROCESS FOR ANALYZING RELAXATION SPECTRA AND RESONANCES IN MATERIALS

[75] Inventor: Jean-Pierre Ibar, Stamford, Conn.

[73] Assignee: Solomat Partners L.P., Stamford, Conn.

[21] Appl. No.: 803,791

[22] Filed: Dec. 6, 1991

Related U.S. Application Data

[63] Continuation of Ser. No. 470,782, Jan. 26, 1990, abandoned.

[30] Foreign Application Priority Data

Jan. 26, 1989 [FR] France .................. 89 00950

[51] Int. Cl.$^5$ .................. G01N 25/00; G01N 27/00
[52] U.S. Cl. .................. 374/045; 374/10; 374/31; 374/53
[58] Field of Search .................. 374/31, 45, 10, 49, 374/32, 46, 33, 53; 73/159

[56] References Cited

U.S. PATENT DOCUMENTS

| | | | |
|---|---|---|---|
| 2,647,393 | 8/1953 | Stewart | 374/49 |
| 2,896,442 | 7/1959 | Bailly | 374/10 |
| 3,271,996 | 9/1966 | Paulik et al. | 374/10 |
| 4,031,740 | 6/1977 | Achermann | 374/31 |
| 4,322,967 | 4/1982 | Seitel et al. | 374/49 |
| 4,566,806 | 1/1986 | DeBondt | 374/45 |
| 4,592,661 | 6/1986 | Wilson | 374/10 |
| 4,761,078 | 8/1988 | Farris et al. | 374/31 |

OTHER PUBLICATIONS

Ibar, J. et al., "Characterization of Polymers by Thermally Stimulated Current Analysis and Relaxation Map Analysis Spectroscopy," Polymer Characterization, Chapter 10 (1990).

Demont, Ph. et al., "Thermally Stimulated Creep for the Study of Copolymers and Blends," Polymer Characterization, Chapter 11 (1990).

*Primary Examiner*—William A. Cuchlinski, Jr.
*Assistant Examiner*—Diego F. F. Gutierrez
*Attorney, Agent, or Firm*—Seidel, Gonda, Lavorgna & Monaco

[57] ABSTRACT

The present invention relates to the use of thermal stimulated processes for analyzing relaxation spectra and resonances in materials. The process is characterized in that at least two coupled excitation fields are applied to the sample of material analyzed along with a programmed temperature variation, with the objective to deconvolute during the thermally stimulated recovery stage the global deformation resulting from the excitation stage, i.e. obtain one by one the individual and elementary relaxation motions responsible for the global deformation, whether these elementary internal motions be of mechanical, electrical or magnetic origin. The process is characterized in the fact that the relaxation spectra for the motions resulting from the coupling between mechanical and electrical (and/or electromagnetical) excitations are obtained at the same time and are inter-related.

7 Claims, 1 Drawing Sheet

PROCESS FOR ANALYZING RELAXATION SPECTRA AND RESONANCES IN MATERIALS

This is a continuation of application Ser. No. 470,782 filed on Jan. 26, 1990 now abandoned.

FIELD OF THE INVENTION

The present invention relates to the use of thermal stimulated processes for analyzing relaxation spectra and resonances in materials by application of programmed disturbances of the internal state of the material, during the excitation stage, and by the study of the thermally stimulated recovery of these deformations, during the return to equilibrium stimulated by heating.

BACKGROUND OF THE INVENTION

Such thermally stimulated processes are already well documented in the literature (Chapter 10 in the ACS Book *Polymer Characterization*, "Characterization of Polymers by Thermally Stimulated Current Analysis and Relaxation Map Analysis Spectroscopy, by J. P. Ibar, et al., Polymer Characterization Advances in Chemistry Series No. 227, Edited by Clara D. Craver and Theodore Provder; and for the TSCR: Chapter in the ACS Book *Polymer Characterization*, "Thermally Stimulated Creep for the Study of Copolymers and Blends" by Philippe Demont, et al.). The aim of such processes, which will be examined in greater detail hereinafter, is to understand the behavior of materials by studying the relaxations and internal motions which take place in order to optimize their mechanical, electrical, magnetic, etc., performances.

More generally speaking, the recovery process of a system applies to the phenomenon of recovering its initial state, after the application of a deformation has taken the system out of equilibrium. The recovery process is stimulated by a (linear) temperature increase, or can occur isothermally over time. Relaxation phenomena in materials during recovery are the results of internal motions due to disturbances either of a mechanical, electrical, magnetic or electromagnetic nature. Materials processed in industry have physical properties which depend on the ability to have local motion within the internal structure irrespective of whether this motion occurs at the level of the molecules, the atoms, or the macromolecules (for polymeric materials), or at the sub-atomic level. Deformation at one level or the other depends upon the type of excitation field involved to bring the material out of its equilibrium state at a given temperature.

Essentially, three types of methods for studying relaxation phenomena and resonances can be distinguished: (1) resonance methods, (2) damping analysis methods and (3) heat stimulated methods. In the resonance method, the material is subjected to a periodic excitation at a fixed frequency of a mechanical, electrical or magnetic nature at a determined temperature and fixed pressure. The periodic excitation frequency can be adjusted to enable the determination of the resonance frequency for this temperature and pressure. The frequency of resonance corresponds to the frequency of the internal motion occurring under these conditions. An alternative method, which is frequently used, consists in subjecting the material to an excitation at a determined frequency and programming a variation in temperature. When the temperature reaches a level capable of allowing the internal movements sought to be characterized, a resonance peak for the selected excitation frequency is observed. It is possible to operate at various (fixed) frequencies and thus analyze the dependence between frequency and temperature which provides access to the mechanism responsible for internal motion under investigation.

In many instances, the internal motion is kinetically controlled, and the variation in the resonance peak frequency (fm) varies with the maximum temperature of the peak Tm, and the results are often collected as the ln (fm) versus 1/Tm, a so-called Arrhenius diagram (Tm is in degrees Kelvin and ln is the natural logarithm). The linearity of the Arrhenius line is indicative of an activated phenomenon. The slope of the straight line in the Arrhenius diagram is related to the activation enthalpy of the process due to internal motions and the intercept is proportional to the activation entropy, i.e., to the jump frequency between the activated states allowing motion. By determining the values of the entropy and enthalpy, one can determine the origin of the movements occurring inside the material irrespective of their origin, whether it is viscous, atomic or sub-atomic. Mechanical deformation fields allow movements of the viscous type to occur in the material (so does ultrasonic excitation) and electrical fields (voltages) applied to the material allow the study of motions related to the electronic interactions between the atoms inside the material. The sub-atomic movements are delocalized by applying electromagnetic excitations.

In the characterization processes which are the subject of this invention, the temperature program is always the same regardless of the origin of the excitation, and consists of exciting the material at a particular temperature, then quenching it, interrupted by partial isothermal relaxation if necessary, and finally heating it up linearly to "develop" the response to the excitation stage during a thermally stimulated return to equilibrium.

The analysis methods using damping in the material consist in the application of a deformation of the material for a given length of time at a given temperature, cutting off the source of the excitation and analyzing the return to equilibrium (recovery curve) at that temperature by recording the freely oscillating damping curve. The equation of the recovery curve gives direct access to the damping factor at that corresponding temperature. The frequency of the oscillation and the damping factor relate to internal friction, and provide the relaxation time at the corresponding temperature. The frequency of oscillation and the damping factor vary with the temperature at which the material is being deformed. This enables the determination of the damping factor at different frequencies and different temperatures. As above, the origin of the internal motions may be found by studying the corresponding Arrhenius diagrams in plots of log of ln (fm) vs. 1/Tm The so-called "thermal stimulated" methods comprise purely calorimetric methods and methods combining the influence of temperature and a "stimulant" variable which may be a mechanical, electrical or an electromagnetic variable. Differential scanning calorimetry (DSC) consists in comparing the calorific energy flux supplied to two crucibles located in the same thermostatic atmosphere, a device in which one of the two crucibles contains the material to be analyzed. The temperature in the chamber may be programmed to increase, decrease, or to stay constant (isothermal mode). In a DSC the calorimeter is servo regulated in such a way that the temperature of the two crucibles is exactly the same. The variable energy flux supplied or subtracted from the crucibles is recorded as the temperature of the cell varies, or as a function of time under isothermal conditions. Differential Thermal Analysis (DTA) is a slight variant of this microcalorimetric DSC process, for which the fine difference in the temperature between the two crucibles is recorded as a function of the cell temperature. The difference in the temperature between the two crucibles changes when there is an alteration in the physical structure or in the physical and/or chemical structure resulting in the variation in enthalpy within the material. In a DSC analysis, the energy flow differential to maintain the two pans at the same temperature is recorded, and a peak is observed when there is a modification in the thermodynamic state of the material. The peak characteristics relate to the state of the material, and transcribe the extent of internal motion and local reorganization, for instance due to molecular relaxations. Differential scanning calorimetry is a rapid and streamlined method of determining phase transitions in materials, for example in order to determine fusion and solidification temperatures, and the glass transition temperature in the case of the amorphous phase of non-crystalline or semi-crystalline materials. It should be noted that in this characterization technique, temperature essentially plays two roles, that of stimulator by contributing thermal energy capable of initiating activated internal motions, and that of sensor, by comparative measurements of the temperature or the flow of energy of the two crucibles, one containing the material to be characterized.

One variant of this process consists in obtaining calorific heat capacity curves as a function of the temperature at different atmospheric pressures.

Atmospheric pressure plays an important role with respect to the kinetics of relaxation phenomena. It is presently known that an increase in pressure is accompanied by a restriction of internal movements, which is observed in differential microcalorimetry by an increase in the temperature at which the internal movements are released during a thermal analysis. Apparatus currently marketed enable microcalorimetry curves to be obtained at pressurized atmospheres. The pressure remains constant during the heating or cooling cycle of these analyses. It is one of the characteristics of the present invention to provide means to submit the crucibles and their content to a pressure history treatment to enable the fine characterization of internal motions inside the material under investigation.

A further important type of analytical instruments for measuring internal movements in materials by the thermal-stimulated effect is described in the works of several authors, and concerns thermal-stimulated current techniques (TSC), and thermal-stimulated creep techniques (TSCR). These techniques are relatively original with respect to the previously described techniques. In these techniques temperature plays the role of developer while the external variables imposed during the excitation stage play the role of "marker".

In a variant of the process, described in further detail hereinafter, temperature also plays the role of "filter" for the relaxation times; this is the "thermal-windowing" filtering method. The aim of the excitation, in the form of a mechanical, electrical or magnetic field, etc., imposed on the material at a given temperature, is to induce orientation, or more generally to cause an imbalance in the system, by the effect of the field on the free activation energy value. The field intensity imposed remains fixed for a given time, the time for the new state of equilibrium to establish itself, and the temperature is lowered very quickly (tempering) to a temperature at which the new thermodynamic state of the material is no longer able to modify itself, for kinetic reasons; consequently a "frozen-in picture" of the state obtained at high temperature is produced. Analysis by the thermal stimulated effect consists in suppressing the field at low temperatures and reheating the material, which is now free of all stresses, and in so doing freeing up the internal motions which are thermally activated to allow their return to equilibrium. The kinetics for the return to equilibrium, induced by the temperature, can be analyzed quantitatively and is a function of the processing parameters of the material and its chemical structure. It is also a function of the morphology.

The thermal stimulated effect reveals all the relaxation modes occurring in a global manner. If the local motions inside the material are not simple in the sense of a pure relaxation of the Debye type, or when there is a large degree of interactive coupling between the relaxation modes responsible for the global response of the material, it is then very difficult to attribute to the recovery curve any particular local motion occurring in the material. Since the entire response of the material to a given excitation is global, it is generally essential to deconvolute the global response and define the relaxation time distribution, corresponding by analogy to different coupled resonators. The coupling between the elementary modes of relaxation is subject to a specific kinetics, itself a function of structural, chemical and morphological parameters. The description of the elementary modes, their thermo-kinetic characteristics (activation energy and entropy) and the description of the coupling is essential for understanding the macroscopic properties of materials. The TSC (thermally stimulated current) and TSCR (thermal stimulated creep processes) are thermal stimulated techniques which use the application of a field, either electrical (for TSC) or mechanical (for TSCR) at a given temperature in order to orient the dipoles in the material (TSC) or the chain segments (TSCR), with the aim of disclosing their individual existence when heated up in a controlled manner after cooling, and after the application of the field has been removed.

The two techniques, TSC and TSCR, have been described in the literature (for the TSC: Chapter 10 in the ACS Book *Polymer Characterization*, "Characterization of Polymers by Thermally Stimulated Current Analysis and Relaxation Map Analysis Spectroscopy, by J. P. Ibar, et al., Polymer Characterization Advances in Chemistry Series No. 227, Edited by Clara D. Craver and Theodore Provder; and for the TSCR: Chapter in the ACS Book *Polymer Characterization*, "Thermally Stimulated Creep for the Study of Copolymers and Blends" by Philippe Demont, et al.).

The principle of the thermal stimulated windowing technique is summarized herewith. The technique has been used a great deal by the scientists of the Laboratory of Physique des Solides in Toulouse, France. These researchers, headed by Professor Lacabanne, concentrated on the application of the thermal windowing method with the aim of isolating one by one the individual relaxations making up a cooperative complex spectrum. The method consists in applying an excitation field (electrical *or* mechanical) to induce orientation in the material at a selected temperature of excitation $T_p$. The temperature is subsequently lowered by a few degrees, with the field still applied. At that temperature $T_d$, the excitation field is then removed and the material is free to return to its state of equilibrium at this temperature $T_d$. However, it can only do so for a small time $t_d$ and therefore the material cannot relax completely at $T_d$, and the remaining orientation induced in the material is then frozen in by quenching to a very low temperature $T_0$. The subsequent reheating at a controlled heating speed, discloses the elementary kinetics of the relaxation mode isolated in the window temperature range $(T_p - T_d)$. The curve obtained during this recovery stage at a constant rate of heating is of a Debye nature, which may be analyzed directly and quantitatively according to the Arrhenius formulation to determine the activation enthalpy and activation entropy parameters for this isolated deconvoluted elementary relaxation. By changing the value of $T_p$ around the global temperature peak observed in either TSC or TSCR, all the relaxation modes co-operating in an interactive manner and contributing to the global response observed without thermal windowing can be isolated one by one. This represents the description of the prior art according to the processes described as thermal stimulated processes.

However, these known methods for analyzing and characterizing materials by the thermal stimulated effect have major negative drawbacks: the method using thermal stimulated current cannot be applied to conductors or semiconductor materials for which the electrical resistance is smaller than $10^7$ ohms/meter of thickness; the method using thermal stimulated creep is not easy to apply to pasty or liquid materials and does not allow temperatures close to the fusion point of the materials to b reached; and there is no simple correlation between the distribution spectra for the relaxation times obtained by TSC and TSCR analysis. This is a major drawback which casts a doubt on the validity of the results obtained by these techniques. The relationship between the mechanical and electrical spectrum of relaxation appears to be complex. In addition, the thermal stimulated method presented in the prior art appears to disturb the structural state of the sample owing to the very nature of the experiment itself: the TSC or TSCR methods consist in applying an electrical or mechanical field at a temperature $T_p$ in the vicinity of the temperature at which the internal motions occur. The effect of bringing the material to this temperature $T_p$ enables the latter to relax from its internal stresses, if there are any present, or to modify its morphology, if it is capable of crystallizing, or even modifying its degree of curing for curable materials and thermoset resins. It is therefore clear that thermal stimulated processes are restricted to the study of internal motions undisturbed by morphological changes at the analysis temperature $T_p$.

It is an object of this invention to add a variable to the existing prior art in order to remedy that important drawback by the use of windowing processes which do not alter the morphology the way thermal-windowing does, as will be explained hereafter. In other words, it is a characteristic of the present invention to describe an excitation field profile which rheologically freezes the material at a constant given temperature instead of changing the temperature in order to create the window necessary to induce the filtering process (thermal windowing).

The main disadvantage of differential microcalorimetry or of differential thermal analysis is that the instrument response is a global response which integrates the co-operative plurality of internal relaxations. A further main disadvantage is the low sensitivity in detecting "secondary" internal movements for which the activation enthalpy is low. Finally, this technique also presents difficulties, especially a lack of sensitivity, in studying certain phenomena such as the orientation of plastic materials or the physical aging phenomena. For instance, it is not rare to observe great variations in the mechanical properties of plastic materials and not to lack such evidence of any difference on the basis of the corresponding traces in DSC analyses. Differential microcalorimetry appears not to be very sensitive to internal stresses relaxed kinetically during physical aging.

A further major disadvantage of the thermal stimulated processes described in the prior art is that the sample must be changed for each temperature $T_p$ when the object of the analysis is to study physical aging or internal stresses. This results in a long and expensive analysis process. In the prior art, a technician using the TSC analysis cell or TSCR analysis cell must prepare a variety of samples and introduce them in succession one after the other. The thermal windowing experiments are then run according to the previous description and a new sample has to be entered into the chamber for each $T_p$ since the sample which has been analyzed has lost its initial condition, which is what is being studied. The above procedure is repeated for each excitation temperature $T_p$ with a new sample until the complete relaxation spectrum is obtained. This method of analysis for isolating simple modes in materials having internal stresses requires a large number of samples and a great deal of labor.

A further major disadvantage of the prior art is that the TSC and TSCR cells are different and the two techniques cannot be used simultaneously on the same sample.

SUMMARY OF THE INVENTION

It is an object of the present invention to remedy these problems and provide means to analyze the mechanical and electrical spectrum for a given sample.

It is also an object of this invention to provide means to characterize several samples simultaneously in order to allow the technique to adapt to the situation of a change in the internal structure of the material with the change of temperature of excitation $T_p$.

Analysis methods based on resonance and internal damping are "global" methods which do not enable elementary relaxation modes to be isolated one by one, and very often the apparent activation energy which is obtained from the Arrhenius diagrams (ln fm vs. 1/Tm) is frequently too large to be realistic, which reveals the fact that the internal motions observed in a global peak are in fact coupled and that the response of the apparatus results from a cooperative coupling between a plurality of relaxations acting globally. This implies a major drawback of the resonance and damping methods in their attempt to give an interpretation to the origin of internal motion. It should be mentioned that the thermal analysis processes described as prior art in the literature (TSC, TSCR) are capable of reconstructing the global response of the material from the thermal windowed experiments, and therefore calculating the resonance curves and damping characteristics of the material, i.e., providing the same output as the more traditional thermal analysis equipment. This is why the process of this invention is said to be capable of providing both the spectra of relaxation of a given material, and the characteristic resonance at any given frequency or temperature, by calculation from the spectrum of relaxation.

An object of the present invention is to overcome the disadvantages of the known processes described in the prior art as thermal stimulated processes and the invention proposes to create an efficient process which can be applied in a relatively general manner to a large number of materials and to a large number of transitions in materials enabling the analysis to be carried out either to characterize mechanical, electrical, magnetic or electromagnetic transitions. To this end, the invention concerns a process of the type mentioned in the description of the prior art as thermal stimulated processes, but characterized in that at least two coupled excitation fields are applied to the sample of material analyzed. In accordance with a further characteristic of the invention, the excitation fields are selected from the group consisting of electrical excitation fields (ac or dc voltage), mechanical excitation fields (hydrostatic pressure, force, shear stress, oscillating or static), magnetic excitation fields, or electromagnetic excitation fields (ac or dc). According to a further characteristic of the invention, the variables which are used as output to characterize the resonance and relaxation behavior of the material are chosen from among the current, strain rate, the stress rate, and the energy flux differential to keep two crucibles at the same temperature.

According to a further characteristic of the invention, if the invention applies to a micro calorimetric device such as a DTA or a DSC, the special characteristics consist in detecting the changes between at least two samples (one being used as a reference) which are assigned constantly the same temperature but which are subjected to two thermal pressures.

As a sub-characteristic of the above-mentioned process, the pressure in the crucibles' chamber changes in time according to a predetermined program.

DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1C:
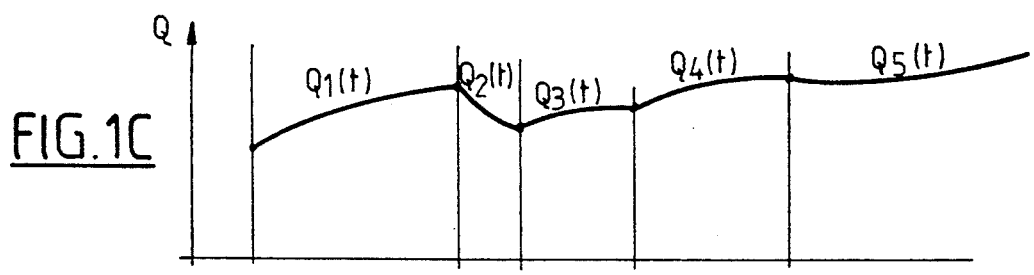
FIGS. 1A, 1B and 1C are representative curves of a temperature program, a first excitation field P(t) and a second excitation field Q(t), respectively.
Figure 1B:
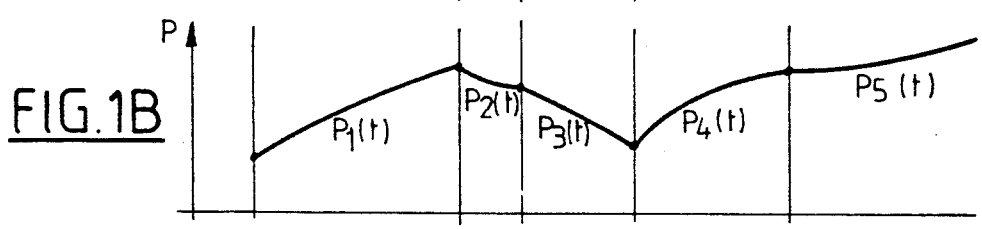
Figure 1A:
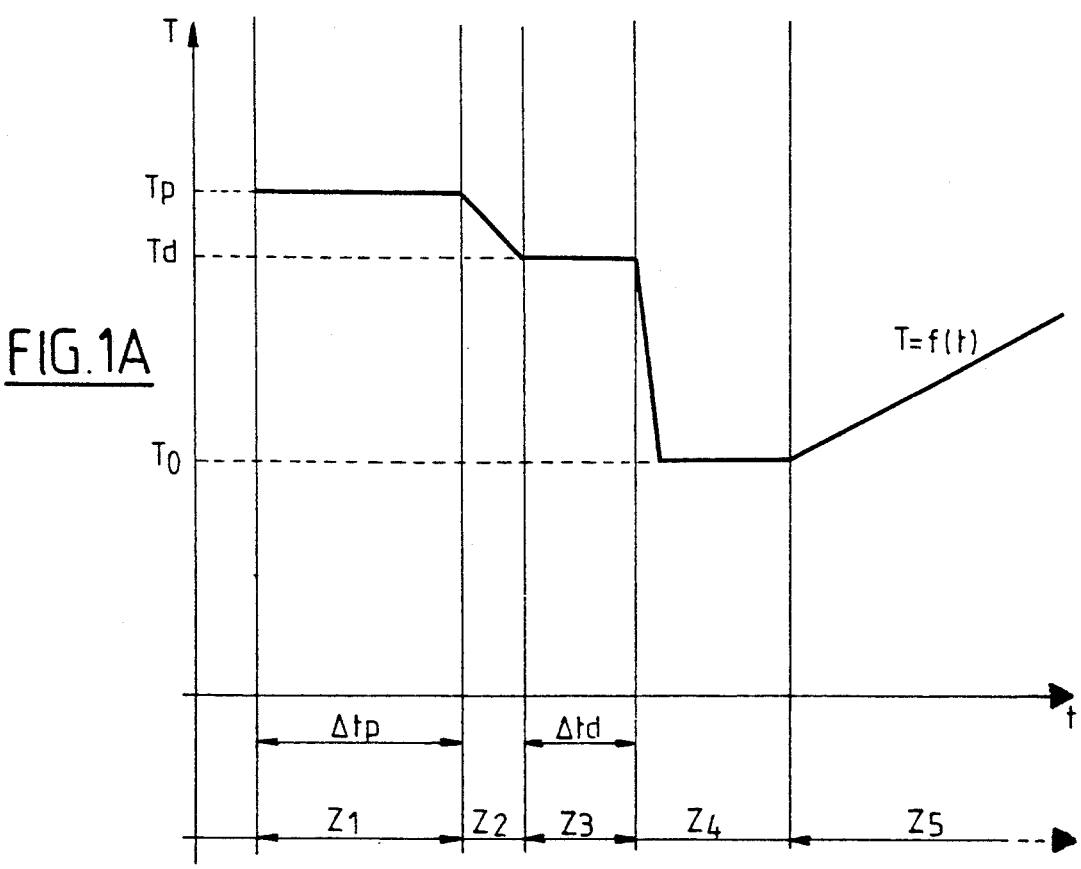

According to one of the characteristics of the invention, the temperature T varies according to a predetermined program which may be divided into several intervals, for instance five zones—Z1, Z2, Z3, Z4, Z5, as shown in FIG. 1A. Thus, during the analysis, the temperature evolves in a manner which is programmed, for instance by means of equipment capable of PID controls.

During this variation of the temperature, the material sample is subjected to the action of at least two excitation fields P(t) and Q(t) shown clearly in FIG. 1B and FIG. 1C. The variation of P(t) and Q(t) is coupled and the coupling depends on the transition characteristics that the user has selected to analyze. The excitation fields vary with time t in a programmed manner.

In each zone, Z1 to Z5, the evolution of each of the excitation fields P(t) and Q(t) is represented by the corresponding curve sections in each zone—P1(t), Q1(t); P2(t), Q2(t); P3(t), Q3(t); P4(t), Q4(t); P5(t), Q5(t). The different curve sections may be continuous or discontinuous depending on the material analyzed and the nature of the analysis. The type of the excitation fields applied to the sample may be either electrical, magnetic, electromagnetic or mechanical. The force exerted on the material might be a magnetic, mechanical or a hydrostatic force. The selection of the type of forces and fields depends on the nature of the transition which is to be characterized.

The excitation fields are coupled in order to isolate the elementary Debye modes of relaxation which contribute to the global response. In a further embodiment of the temperature variation according to the present invention, the temperature varies as a function of time according to a program similar to those described in the thermal stimulated methods TSC and TSCR. Thus the sample of material analyzed according to the process described in the invention, is heated to an excitation temperature $T_p$ at which the sample remains for a length of time $t_p$. Subsequently, this temperature is lowered by a few degrees in order to arrive at the depolarization temperature $T_d$. The sample remains at this temperature for the duration of time represented in FIG. 1A by zone Z2. At the end of this recovery period at $T_d$, the sample undergoes thermal quenching in order to lower its temperature to the freezing temperature $T_o$, and from this temperature a linear variation of temperature $T = f(t)$ is applied. This temperature profile would be a characteristic of the invention in FIG. 1A, according to this embodiment of the invention. However, the process, according to the present invention, differs from the prior art in that it superimposes the effect of at least two excitation fields as the temperature variation program changes. The objective is to create a filtering of the various relaxation modes by means other than pure thermal-windowing effects. Variables which are capable of individually modifying the recovery kinetics associated with local internal movements in the material can be coupled in the process described here to create the desired filtering effect.

Owing to the coupling between several types of excitation modes and the resulting effect it has on the spectrum of relaxation, the present invention enables the understanding and the decoupling of the interactions between local movement occurring in the material, such as dipolar relaxations, and the global movements, such as the mechanical induced or viscous relaxations. The new process according to the invention makes it possible to characterize such a coupling between the global aspect of the deformation and the local aspect. For example, in one embodiment of the invention, an electrical voltage field applied to a material at a given temperature is coupled up to a mechanical field applied to the material at the same time. The mechanical variable may be either a hydrostatic pressure or a stress tensor. The variable, as measured during recovery, may either be the electric current produced by the material during heating or in isothermal condition, or the strain displacement as resulting from recovering the effect of deforming the material at $T_p$, or both of these at the same time. Coupling between applied excitation fields enables one to sort out the origin and the differences between the dielectric relaxation resulting from electrical motions and the mechanical relaxation due to viscous motions. The coupling laws between these internal motions due to either viscous causes and electronic interactive causes can thus be determined according to this characteristic of the invention. The excitation profiles P(t), Q(t) describe how to apply the excitation fields such as to bring the material out of equilibrium, and back to equilibrium as a function of T. The excitation profile of the fields may be identical or different so as to demonstrate one or another particular characteristic of the recovery kinetics. This explains why there are many types of profiles for the two fields variations P(t) and Q(t). Each profile of P(t) has to be programmed in and coupled with the program used for Q(t) in order to determine an excitation history, which then enables decoupling of both dielectric and mechanical relaxation giving rise to a global answer in the material.

In another embodiment of the invention, the pressure in the measuring chamber of a TSC or TSCR analysis apparatus varies according to a program and is coupled either with the voltage field (in the case of TSC) or with a force field (in the case of stress of TSCR). In the case of the application of an electromagnetic or magnetic field to excite the sub-atomic structure of magnetic materials, the pressure will be coupled with the magnetic field itself. In the particular case of coupling pressure effect with another field, the pressure plays a role identical to temperature, in particular in the creation of a windowing effect ($P_d - P_p$) with the aim of isolating rheologically simple relaxation modes. For instance, at $T_d$, temperature of partial recovery, the pressure may be increased to delay the recovery of a given set of relaxation times influenced by the effect of both pressure and temperature. Release of the pressure, still at $T_d$, results in the recovery of the relaxation modes which have not yet relaxed due to the effect of pressure. In the case of an electrical field coupled with pressure, if the motion of the dipoles activated by the excitation voltage is influenced by a pressure effect, the pressure/voltage field coupling enables one to obtain the full relaxation spectrum in a much more rapid manner than for a classical normal TSC analysis, as described by the prior art. In other words, the "thermal windowing" may be carried out by other means than lowering the temperature. In this case here, the window is created by a pressure effect which offers the additional advantages of being fairly easily implemented, and also the window width can be very small, resulting in an increase resolution to resolve the elementary peaks.

In the above illustration of a preferred embodiment of the invention, hydrostatic pressure is shown as a variable capable of stimulating a change of state in the material around a phase transition, but the application of a mechanical, electrical or electromagnetic vibration may serve the same objectives. The application of a vibration to a material induces changes in the value of the phase transition temperature, due to modification of the internal state of the material. For instance, the transition temperature increases as the vibration frequency increases (a phenomenon well known to material scientists and rheologists working with relaxation phenomena). The phenomenon of increasing the temperature at which a transition occurs for a given material is equivalent to a lowering of the temperature with respect to the transition temperature. In other words, by changing the position of the temperature of the phase transition at a given temperature, by vibrational means, one is able to change the window width between the temperature of the test and the transition temperature under investigation. For activated phenomena, an increase in the vibration frequency between two activated levels is equivalent to a decrease in temperature. Again, this effect may be used to define the "windows" similar to those created with the thermal windowing method used by the prior art. Coupling thermal windowing effects (which are created by pure changes of temperature) and "frequency or pressure simulated" windows (created by the action of a vibrating field or by the effect of changing the hydrostatic pressure) enables one to characterize the local motions with respect to their origin, whether it be of viscous or electronic interactive nature.

It should be noted that the nature of the vibration applied during the excitation state (either at temperature $T_p$ or during the recovery at $T_d$) may be identical or different from the nature of the static field, applied in conjunction to it in order to create the coupling, and that the detecting variable during the sensing stage (during the programmed rise in temperature to reveal a relaxation mode in the recovery zone) may be of the same nature as the vibratory variable or the static field. For example, it is possible, in another embodiment of this invention, to use coupling between a mechanical field (hydrostatic pressure or a shear stress applied during a time $t_p$ at temperature $T_p$) with a vibratory field of electrical nature or of electromagnetic nature (with a predetermined frequency and amplitude of vibration), that vibratory excitation being applied at $T_p$ or at $T_d$ for a programmed time. The recovery curve may be studied either with electric variables (in such a case a measurement of the depolarization current is performed), or with a mechanical variable (variation of the strain and strain rate during recovery), or lastly with a purely thermal measurement (measurement of the heat capacity changes during recovery).

In a particularly important embodiment of the invention, heat sensing means such as those used in a DSC or a DTA are used to detect motions during the recovery stage, after an initial excitation stage which comprises thermal and pressure windowing to filter out singular relaxation modes. The cell chamber which includes the samples to be analyzed is divided into two compartments, one at pressure $P_1$, the other at pressure $P_2$. The two compartments are strictly at the same temperature irrespective of the temperature program T in FIG. 1A, or the pressure in each compartment, whether this is during the excitation or the recovery phase. In a particular embodiment of the above arrangement, only two crucibles are located in each compartment, one of the crucibles in each compartment containing a sample of the material to be analyzed.

It is believed that those skilled in the art will understand how to adapt a DSC or DTA apparatus as described in the forgoing paragraph and, accordingly, an illustration of such a modified apparatus is believed superfluous.

In a variant of the previous embodiment, the compartments may contain a plurality of crucibles, each containing a sample of the material to be analyzed in addition to a control reference sample. This configuration is particularly suitable for studying physical aging phenomena and curing or crosslinking or crystallization phenomena, or for studying the state of internal stresses in the material. Note that in this embodiment of the invention, a single run will provide the measurement of several samples at once and submit it to the same temperature variation.

The rate of change of the microcalorimetric differentials between the several samples and between the crucibles are automatically recorded regardless of the compartment they are in and the temperature or pressure which is programmed to vary. The temperature and pressure variations inside the cell chambers are programmed by a computer to create windowing effects which make it possible to separate out the singular relaxation modes, provided that the relation occurring by the change of temperature or pressure result in a modification in the heat capacity or the enthalpy of the material. The microcalories supplied to the crucibles may be compared for the crucibles located inside the same compartment or for crucibles containing samples of identical origin but located in two different compartments and therefore at different pressures. The analysis of the enthalpy difference leads to the characterization of the distribution of enthalpies attributed to a spectrum of relaxation modes.

In another embodiment of the invention, the pressure may be programmed in a specific way to rapidly study the kinetic characteristics of a pressure sensitive phase transition, such as the glass transition temperature of glass forming materials. The action of hydrostatic pressure on the material may be used to "create" at will a transition effect, since the transition itself occurs at a higher temperature if the pressure is suddenly increased in the chamber. The sample, which is slowly heated up, is subjected to rapid pressurization (simulating quenching across the transition under investigation), resulting in states across the transition temperature, and subsequently depressurized at a controlled rate in order to analyze the kinetic curve of the change of state during the return to equilibrium, since the effect of relaxing the pressure will be to cross the transition in the other direction, giving an opportunity to record the kinetic changes occurring during this partial return to equilibrium. The temperature changes during that process can be slow enough to be considered constant and therefore the process can correspond to the study of a recovery return to equilibrium under isothermal conditions. This process of pressurizing and relaxing may be performed a number of times during the slow increase in temperature in the chamber, thus providing a series of kinetic relaxation curves which can be analyzed with the classical tools of rheology and relaxation kinetics.

In a further embodiment of the invention, for coupling a mechanical field and a hydrostatic pressure, a plurality of samples to be compared may be introduced at the same time into the cell in order to be subjected simultaneously to the same pressurizing programs and the temperature variation programs. The responses obtained simultaneously for the various samples during recovery enable the differences existing initially in the materials to be compared very quickly and in a single operation. This is particularly useful for studying the internal stresses set in an object, for which these stresses vary from one point of the object to the other owing to molding conditions. For example, in the process used to manufacture compact discs or optical discs by injection molding, it is important to eliminate internal stresses in the direction parallel to the reading laser beam. It is thus of prime importance that the material properties do not vary over time and from point to point in the radial direction. This particular embodiment of the invention can be used for the simultaneous study of a plurality of samples in order to determine an internal stress intensity curve.

In a still further embodiment of the invention, the excitation field applied during the windowing process is electromagnetic or corpuscular, for example luminous or sub-radiating (X ray, gamma rays, UV radiation etc.). This excitation mode may be more suitable for the analysis of thin layers of conductor or semi-conductor materials, such as in the characterization of the electronic behavior of the amorphous component, in particular for testing the structure of energy which the global energy is composed of.

One characteristic of the invention is that the same cell base which is normally used for Thermally Stimulated Current (TSC) measurement can also be used for the apparatus carrying out the means necessary for the present invention. This represents a clear advantage of this embodiment since the same apparatus (with a few modifications) can be used for simultaneous excitation and measurement of thermally stimulated mechanical or electrical relaxation occurring in samples, in order to characterize their internal motion.

In FIG. 1A, the temperature profile is programmed via heating and cooling the conducting gas which constitutes the sample environment. When P(t) or Q(t) of FIG. 1A represents the pressure in the chamber, the conducting gas is put under pressure by external means known to a person skilled in the art. A preferred range for the pressure is between 1 bar and 700 bars, and obviously, the thickness of the wall of the cell is modified accordingly in order to accommodate the larger pressures.

In cases where the signal P(t) or Q(t) is a stress imposed on the sample, a load cell is located outside the cell assembly and is controlled by computer means 12 via the load cell sensor. The stress applied can be a torsion, or a flat force, and the displacement can be measured by optical means (transmitted light), or by means of a LVDT, RVDT, Moire fringes, or capacitance.

The application of the stress on the sample holder can be done by means of a stepper motor. The range of modulus preferred for the material studied here goes from 102 to 1011 dyn/cm$^2$. A preferred embodiment of the invention is to use the stepper motor in direct connection to the sample, which provides the stress on the sample. The strain induced by the stress, and the change of strain during recovery (strain rate) are best measured by means of an encoder disc with a dual laser counting. A preferred embodiment for the encoder consists of an optically polished metal with laser etched markings with a predetermined resolution (typically 10 $\mu$). The encoder disk is preferably of minimum thermal mass, must be supported without friction, and must be able to withstand the heat generation during laser marking as well as the heat that may be transported from the heater area up through the central high modulus shaft to the strain detecting encoder disc.

The temperature of use is preferably between $-150°$ C. to 350° C., (with liquid nitrogen as the coolant) or $-260°$ C. to 0° C. (with liquid helium).

The preferred current detector, when P(t) or Q(t) is a voltage, is an electrometer capable of measuring current as low as 10-17 amperes up to 10-9 amperes.

The excitation of the two coupled signals P(t) and Q(t) is done simultaneously by programming before the experiment the ramps of the signals at given predetermined intervals. Each of the signals (electrical power supply ac and/or dc) and stresses (torsion or flection, or compression) is electronically sensed, conditioned and controlled by PID means to conform to the programmed variation. Such procedure is known to persons skilled in the art of PID controls. A computer is used to record the outputs from the sensors and send signal to the exciters. The data (current of polarization, depolarization, stress on the sample, strain (angular, longitudinal or vertical depending on the type of stress), and its derivative strain rate, are continuously computed and archived on the computer storage medium. The analysis of the data is done as either strain rate versus temperature for the mechanical deformation, or current versus temperature for the electrical signal. The measurements are done simultaneously. The direct outputs provide direct information on the resonance characteristics, either mechanical or electrical, of the material at the equivalent frequency of excitation.

The relaxation spectrum can be calculated by using the method of thermal-windowing, as explained in the prior art, depending on the function T(t) in FIG. 1A.

When ac signals are used for P(t) and/or Q(t), the detecting devices can be such that the ac response of the material is continuously compared with the ac excitation, in order to, during the analysis stage, obtain the variation of the storage and loss moduli and dielectric constant. The use of ac signals during the excitation stage serves, however, another purpose, in the present invention, since its use is primarily to induce windowing effects which will be revealed in the sensing stage, upon recovery when the sample is heated up linearly at the end of the experiment. The use of ac signals is to serve as an additional windowing technique, in the sense described herein. The use of hydrostatic pressure serves the same purpose.

The present invention may be embodied in other specific forms without departing from the spirit or essential attributes thereof and, accordingly, reference should be made to the appended claims, rather than to the foregoing specification, as indicating the scope of the invention.

I claim:

1. A process of analyzing relaxation spectra in materials, comprising the steps of:
   a. varying the temperature of at least one sample of material according to a predetermined temperature program;
   b. applying to the sample at least two coupled excitation fields simultaneously with said temperature program, each excitation field being variable according to a predetermined excitation program co-extensive in time with said temperature program; and
   c. measuring at least one sample parameter representative of the relaxation behavior of the sample during a portion of the temperature program.

2. The process according to claim 1, wherein each excitation field is selected from the group comprising electric excitation fields, mechanical excitation fields, magnetic excitation fields, and electromagnetic excitation fields.

3. The process according to claim 1 or 2, wherein the sample parameter comprises temperature.

4. The process according to claim 3, wherein the sample parameter comprising temperature is measured using a selected one of differential microcalorimetry or differential analysis.

5. The process according to claim 4, further comprising the steps of:
   a. simultaneously varying the temperature of at least two samples according to said temperature program;
   b. maintaining said samples at the same temperature but at different pressures; and
   c. performing said differential calorimetry by measuring simultaneously the temperature difference between said samples and a reference temperature.

6. The process according to claim 5, wherein said different pressures are variable over time according to a predetermined program.

7. The process according to claim 1, wherein the excitation fields are oscillatory fields.

* * * * *